US010478579B1

(12) United States Patent
Elton

(10) Patent No.: US 10,478,579 B1
(45) Date of Patent: Nov. 19, 2019

(54) BLIND INTUBATION DEVICE AND RELATED METHODOLOGIES FOR ENDOTRACHEAL INTUBATION

(71) Applicant: Richard Elton, South Ogden, UT (US)

(72) Inventor: Richard Elton, South Ogden, UT (US)

( * ) Notice: Subject to any disclaimer, the term of this patent is extended or adjusted under 35 U.S.C. 154(b) by 0 days.

(21) Appl. No.: 16/428,344

(22) Filed: May 31, 2019

(51) Int. Cl.
*A61M 16/00* (2006.01)
*A61M 16/04* (2006.01)
*A61M 25/06* (2006.01)

(52) U.S. Cl.
CPC .... *A61M 16/0493* (2014.02); *A61M 16/0497* (2013.01); *A61M 2025/0681* (2013.01)

(58) Field of Classification Search
CPC ............ A61M 16/0493; A61M 16/0497
See application file for complete search history.

(56) References Cited

U.S. PATENT DOCUMENTS

| 4,919,126 A * | 4/1990 | Baildon ............ A61M 16/0488 128/200.26 |
| 6,386,199 B1 * | 5/2002 | Alfery .................. A61M 16/04 128/200.26 |
| 6,470,888 B1 * | 10/2002 | Matter ...................... A61L 2/10 128/207.14 |
| 6,843,769 B1 * | 1/2005 | Gandarias ............ A61B 1/0676 600/185 |
| 9,226,651 B2 * | 1/2016 | McGrath ................ A61B 1/267 |
| 2011/0120474 A1 * | 5/2011 | Daugherty ............ A61M 16/04 128/207.17 |

* cited by examiner

*Primary Examiner* — Bradley H Philips
(74) *Attorney, Agent, or Firm* — Buche & Associates, P.C.; Bryce A. Johnson; John K. Buche

(57) ABSTRACT

Disclosed is an apparatus and method to facilitate insertion of the endotracheal tube into the patient's trachea.

7 Claims, 17 Drawing Sheets

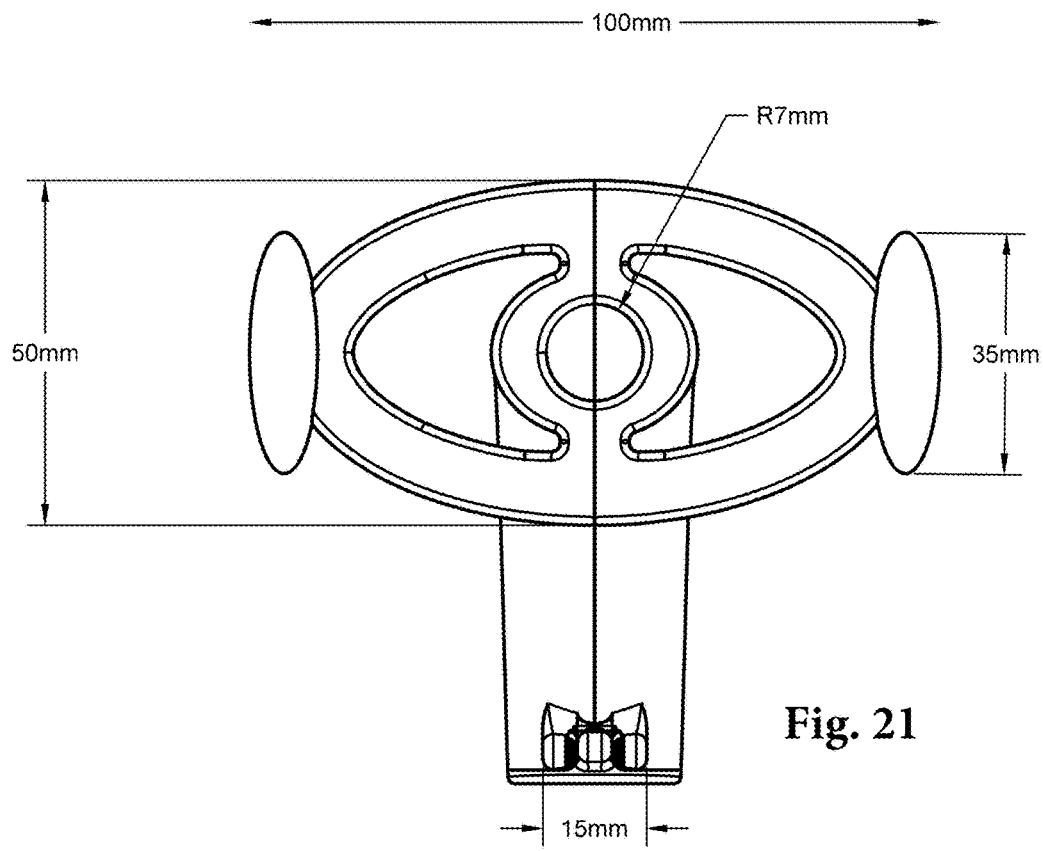
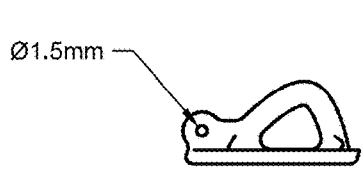
Fig. 22
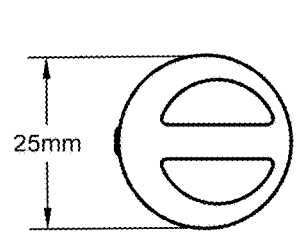
Fig. 23
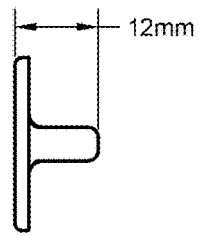
Fig. 24

130°

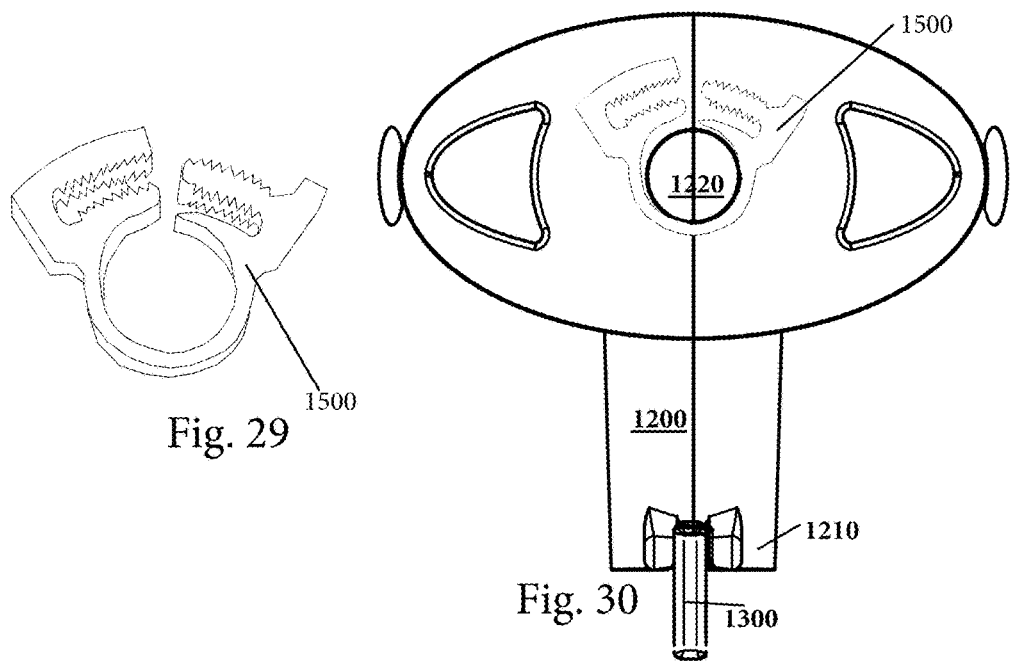
Fig. 29
Fig. 30
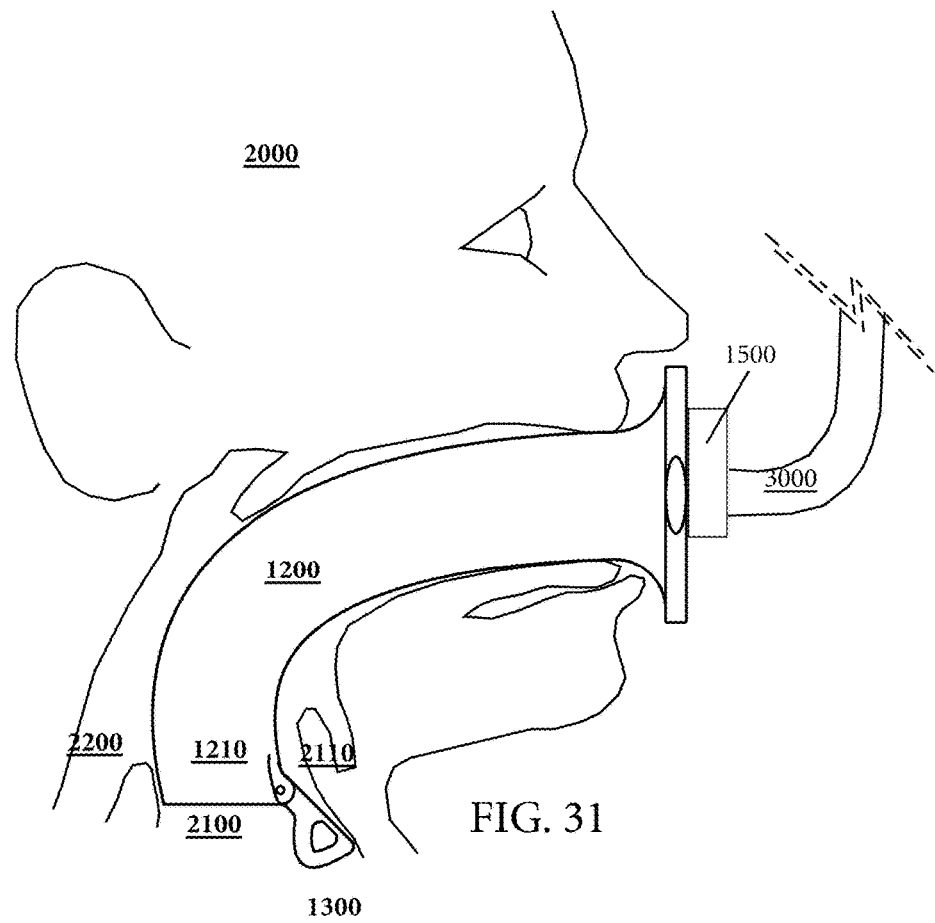
FIG. 31

BLIND INTUBATION DEVICE AND RELATED METHODOLOGIES FOR ENDOTRACHEAL INTUBATION

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

The disclosed subject matter is in the field of apparatuses and related methods of endotracheal intubation.

Background of the Invention

Endotracheal intubation is a medical procedure by which a tube, called the endotracheal tube, is inserted into the mouth and then into the airway (trachea) of a patient. Intubation is a prerequisite to ventilator-assisted breathing and provides a medium through which a ventilator may push air into the patient's lungs. Generally, intubation is employed in the event that a patient is unconscious, e.g., anesthetized, or otherwise requires breathing assistance (for instance, when patients are too sick or injured to breathe on their own or during cardiac arrest). Intubation is always required whenever a patient is given general anesthesia as the sedative paralyzes the patient's diaphragm, but is also employed in the event of respiratory failure including during out-patient surgeries. Patients may also have a temporary or chronic medical condition (e.g., pneumonia or COPD) requiring the use of a ventilator and thus endotracheal tube.

Intubation is a difficult and time consuming procedure. The success of traditional methods of intubation is heavily dependent on the level of skill of the attending physician or technician as proper placement can be difficult to immediately verify and patient harm may occur as a result. If the procedure takes too long, a patient can suffer injuries due to lack of oxygen to the brain.

Conventional methods of intubation favor when the patient is sedated or not fully conscious, allowing for the mouth and airway to relax and thus for easier insertion and placement of the tube. The patient is typically in a prone position immediately prior, and the individual inserting the tube typically stands at the patient's head. The Patient's mouth is opened and tongue is held out of the way while the tube is passed through the patient's throat until it rests within the trachea. When a patient is sedated or unconscious, intubation can take up to 30 seconds to complete by a medical professional in a carefully controlled hospital/clinical setting. If a patient is not sedated, or outside the hospital, intubation can take much longer. For example, outside a hospital during emergency situations encountered by first responders, mass casualty, policemen, firemen, EMT/EMSs, and military, intubation (aka "field intubation") is considered to be "advanced life support" (ALS) and can take more than a minute and thirty seconds to accomplish.

Conventional methods of endotracheal intubation carry the risk of the tube being inadvertently placed into the esophagus rather than the trachea. The risk of tube misplacement is higher during field intubations. See Katz S H, Falk J L. *Misplaced endotracheal tubes by paramedics in an urban emergency medical services system*. Ann Emerg Med. 2001 January; 37(1):32-7 where misplaced endotracheal tubes were found to occur 25% of the time in a study of 108 field intubations. This mistake could hamper or altogether prevent proper respiration. As a result, patients experience heightened risks of brain damage, cardiac arrest, and death, among other things. Any ventilation in the event of misplacement likewise poses serious medical risks. For instance, aspiration of the stomach via the esophagus can result in pneumonia and acute respiratory distress syndrome (ARDS). Further, improper placement of the tube within the trachea may lead to only one lung being properly ventilated, increasing the risk of pneumothorax or inadequate ventilation. Use of the conventional method and apparatus also increases the risk of damaging the patient's teeth, the soft tissue in the back of the throat, and the vocal cords.

Conventional methods of intubation require a laryngoscope handle and blades of varying sizes and shapes, endotracheal tubes, and a means for securing the tube in place. These old means for securing the endotracheal tube in place generally consist of various specially designed commercial products, but less preferable tape and ties are also commonly used as some of the specially designed products can be very costly. Some of the products currently employed consist of assorted masks, bite blocks, and various devices configured to deliver lidocaine to the trachea.

SUMMARY OF THE INVENTION

Accordingly, it is an object of the present disclosure to mitigate the associated medical risks of intubation techniques by providing an apparatus and method to facilitate insertion of the endotracheal tube into the patient's trachea as well as reducing the amount of time taken for intubation (e.g., from 30 seconds to 18 seconds). The disclosed apparatus and technique enables "blind" intubation, i.e., intubation without use of a laryngoscope. It is another object of the present specification to facilitate the insertion of an endotracheal tube at a lower equipment cost than traditional device-assisted or other methods.

In a preferred embodiment, an apparatus for aiding endotracheal intubation comprises:

a funnel with a curved cannulated stem that is configured for oral insertion into a patient's throat;

a lever arm at the tip of the stem;

an endotracheal tube; and, wherein after the curved cannulated stem is orally inserted into the patients throat the endotracheal tube is (a) passed through the funnel and curved cannulated stem to press the lever arm into contact with the patient's epiglottis and (b) directed by the curved cannulated stem away from the esophagus and into the trachea.

In accordance with the present method and apparatus of inserting endotracheal tubes into the patient's airway, the patient is first placed in a prone or substantially equivalent position. The patient's mouth must be accessible to the physician or technician inserting an endotracheal tube. Once the patient is in the proper position, the mouth is opened and the patient's head tilted slightly in an attempt to straighten the passageway from the rear of the mouth to the desired tracheal depth.

The curved cannulated stem of the funnel may then be inserted into the mouth of the patient, preferably but not necessarily with the curvature of the cannulated stem (hook) being orthogonal to the inside of the patient's cheek before being rotated into position. The cannulated stem may preferably have the endotracheal tube already partially inserted, or insertion may take place after the airway has been properly fitted. During rotation of the device into position, the hook, i.e. curved cannulated stem, may be downstream so that the tip of the stem is toward the patient's lungs. Ultimately, the endotracheal tube may be guided past the soft palate and pharynx until it rests fully inserted into the patient's trachea.

The endotracheal tube depresses outward a perforated pad or lever arm as it is passed through tip of the cannulated stem. When so depressed outward, the pad or lever arm holds the epiglottis in place as to reduce the likelihood of esophageal insertion. The cannulated stem may be constructed to safely direct the tube away from the esophagus and into the trachea at a reduced risk of damage to other part of the anatomy and respiratory function. A ventilating means, such as an external bladder or machine lung, is attached the exposed end and funnel portion of the tube.

The manner in which the cannulated stem is inserted greatly reduces the risk of esophageal insertion of the endotracheal tube and thus the risks associated with improper respiration. Some of the associated risks include brain damage, cardiac arrest, and death. Use of the cannulated stem and method at hand likewise reduces the risk of aspiration of the stomach contents or improper lung ventilation and associated risks. Additionally, the simplicity of the apparatus typically allows for intubation in substantially less time than traditional methods.

A preferred method for endotracheal intubation comprising the steps of:
  opening a patient's mouth;
  inserting an cannulated stem into the patient's mouth;
  manipulating the positioning of said stem as to allow for its passage into the throat;
  ensuring the cannulated stem is fully inserted into the patient's throat;
  passing an intubation tube through said cannulated stem into the patient's trachea;
  extending a lever arm from the tip of the cannulated stem to hold the epiglottis out of the way of the intubation tube;
  attaching a ventilating means to the exposed end of the intubation tube; and
  ventilating the patient's lungs.

The present disclosure, both as to its organization and features, may be best understood by reference to the following description taken in conjunction with the appended drawings.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which:

FIG. 21 is a normal view of the blind intubation device;

FIG. 22 shows a schematic view of another embodiment of a lever arm (also called perforated pad);

FIG. 23 shows a schematic view of the lever arm;

FIG. 24 shows a schematic view of the lever arm;

FIG. 29 is a perspective view of a tube clamp 1500;

FIG. 30 is a normal view of the blind intubation device 1000 with a tube clamp 1500 installed on the canal 1220 and the lever arm 1300 extended out of the tip 1210 of the device's 1000 cannulated stem 1200; and, FIG. 31 is an environmental view of the blind intubation device 1000 inserted into a patient's 2000 throat with the curved cannulated stem 1200 turned downstream toward the patient's 2000 trachea 2100, the lever arm 1300 extended from the tip 1210 of the stem 1200 so that it holds the epiglottis 2110 away from the tip 1210 of the stem 1200, a tube clamp 1500 installed on the canal 1220 with a tube 3000 inserted into the canal 1220 and there held fast by the clamp 1500.

Figure 1:
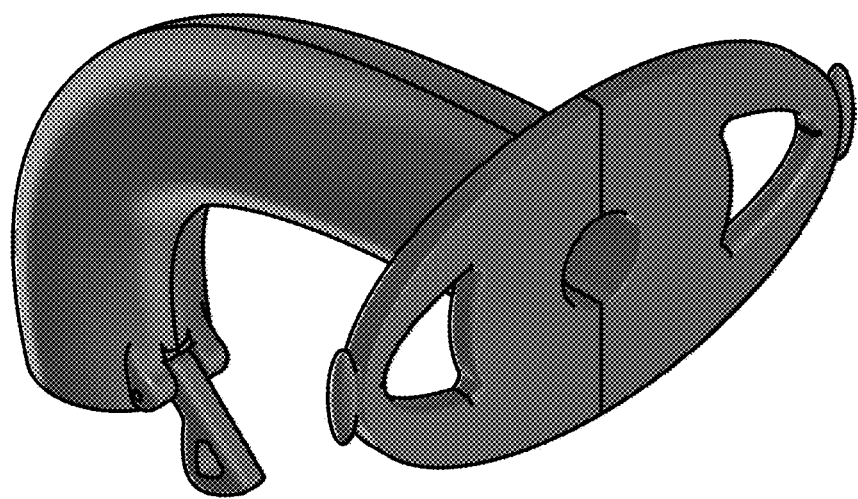
FIG. 1 is a fully rendered isometric view of a blind intubation device 1000.

In the figures, the following reference numerals are associated with the following components of the disclosure;
blind intubation device 1000
funnel 1100
cannulated stem 1200
tip 1210
airway or canal 1220
lever arm or perforated pad 1300
notch 1310
patient 2000
trachea 2100
epiglottis 2110
esophagus 2200

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

Generally disclosed are apparatuses and methods to facilitate insertion of the endotracheal tube into the patient's trachea as well as reducing the amount of time taken for intubation (e.g., from 30 seconds to 18 seconds). The disclosed apparatus and technique enables for "blind" intubation, i.e., intubation without use of a laryngoscope. Hence the device is referred to herein as a blind intubation device. The more specific aspects of the invention are described with reference to the figures.

Figure 2:
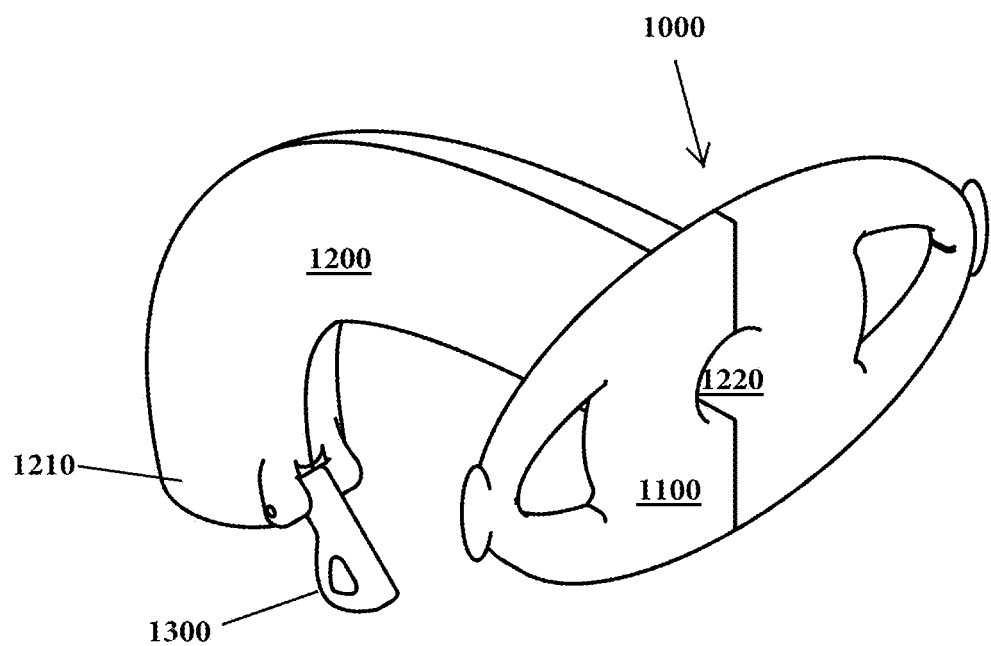
FIG. 2 is an isometric schematic view of the blind intubation device 1000.
Figure 3:
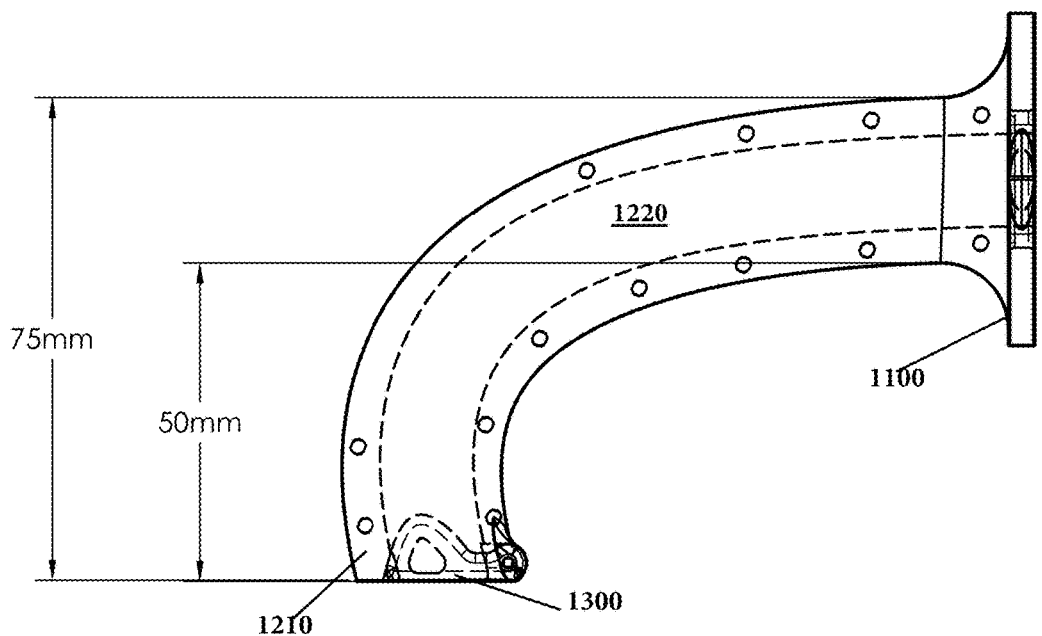
FIG. 3 is a cross-sectional side view of the blind intubation device 1000.
Figure 4:
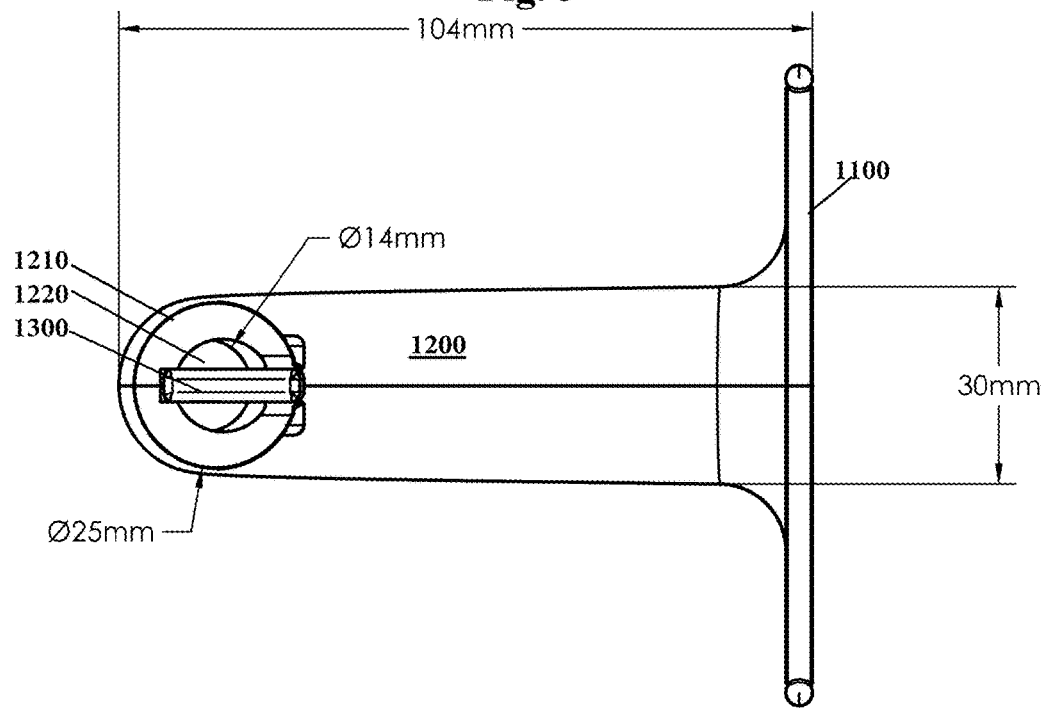
FIG. 4 is front view of the blind intubation device 1000.
Figure 5:
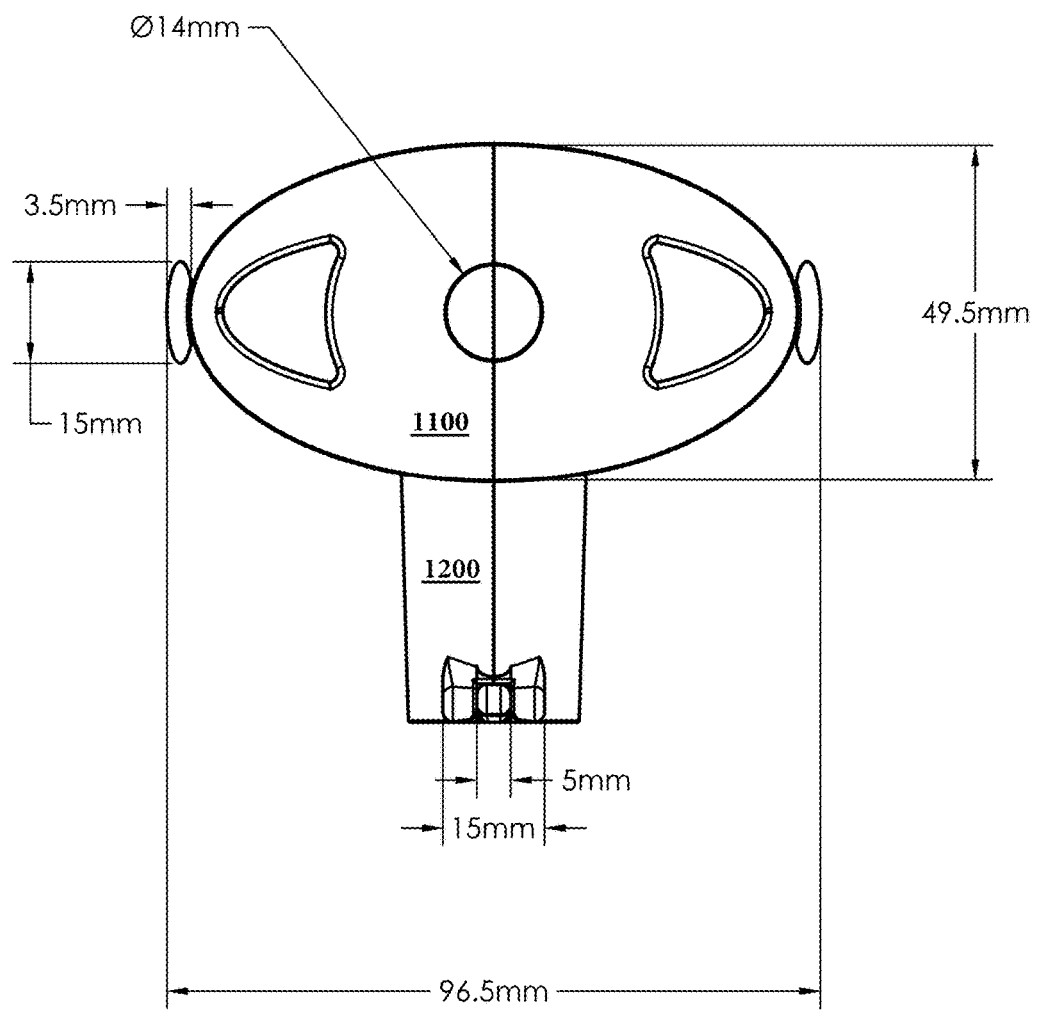
FIG. 5 is a normal view of the blind intubation device 1000.

FIG. 1 is a fully rendered isometric view of a blind intubation device 1000. FIG. 2 is an isometric schematic view of the blind intubation device 1000. FIG. 3 is a cross-sectional side view of the blind intubation device 1000. FIG. 4 is front view of the blind intubation device 1000. FIG. 5 is a normal view of the blind intubation device 1000. As shown in FIGS. 1 through 6 the device 1000 comprises three basic parts:
1. a funnel 1100,
2. a curved and cannulated stem 1200 with tip 1210 and airway between the funnel 1100 and tip 1210, and
3. a lever arm 1300 that is tucked normally tucked into the tip 1210. Suitably, the device may be 3-D printed or molded of plastic. In a preferred embodiment, the device is molded of plastic in two halves and snapped together as shown in FIG. 3. The device may also be made of metal or carved of wood.

Figure 6:
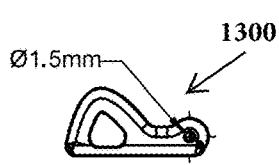
FIG. 6 shows a schematic view of a lever arm 1300 (also called perforated pad)
Figure 7:
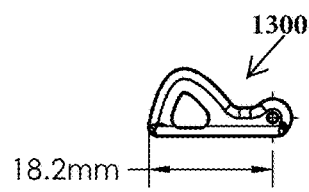
FIG. 7 shows a schematic view of the lever arm 1300.
Figure 8:
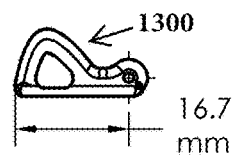
FIG. 8 shows a schematic view of the lever arm 1300.
Figure 9A:
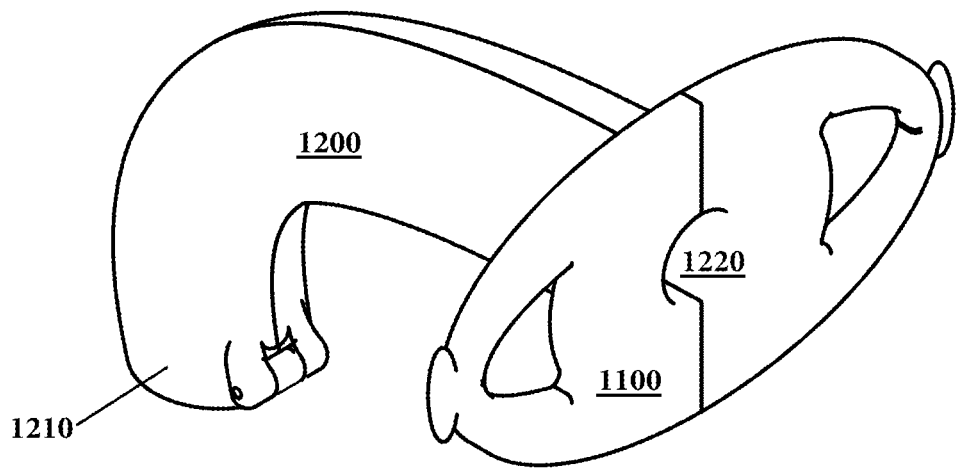
FIG. 9A an isometric schematic view of the blind intubation device 1000 with the lever arm 1300 tucked into the tip 1210 of the device's 1000 cannulated stem 1200.
Figure 9B:
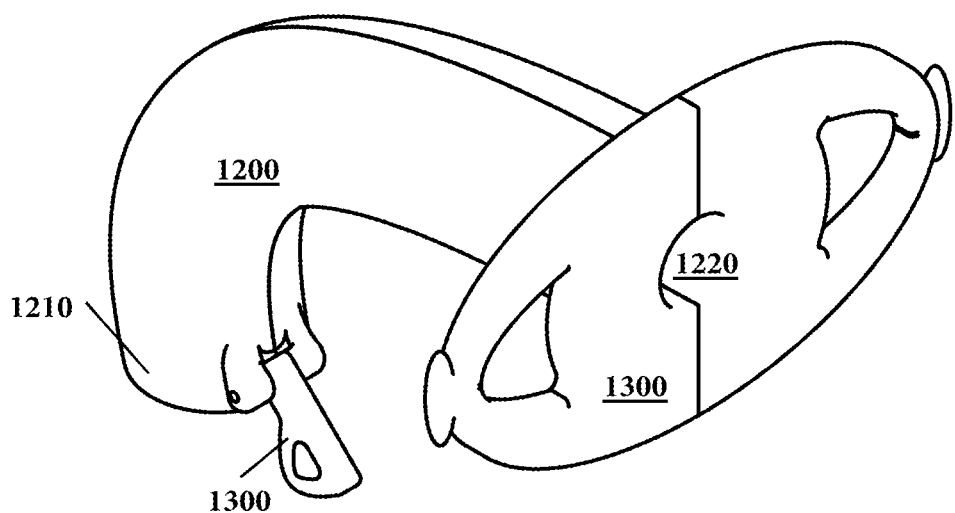
FIG. 9B an isometric schematic view of the blind intubation device 1000 with the lever arm 1300 extended out of the tip 1210 of the device's 1000 cannulated stem 1200.
Figure 10A:
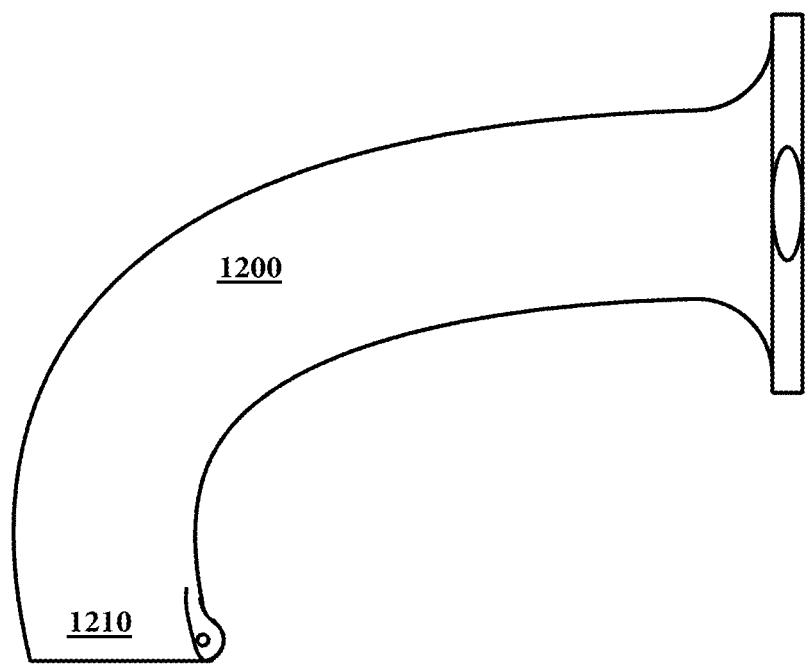
FIG. 10A a side view of the blind intubation device 1000 with the lever arm 1300 tucked into the tip 1210 of the device's 1000 cannulated stem 1200.
Figure 10B:
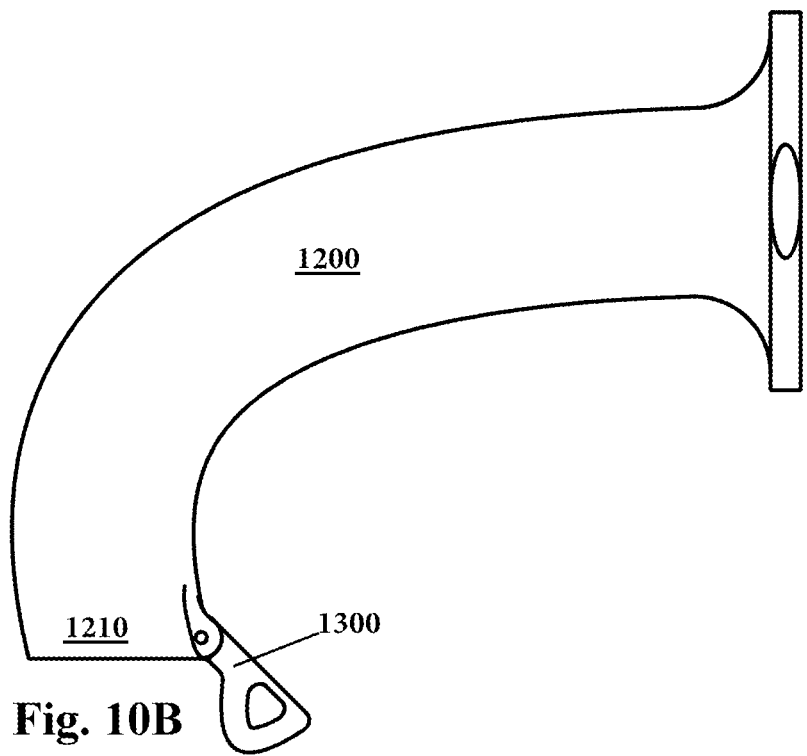
FIG. 10B a side view of the blind intubation device 1000 with the lever arm 1300 extended out of the tip 1210 of the device's 1000 cannulated stem 1200.
Figure 11A:
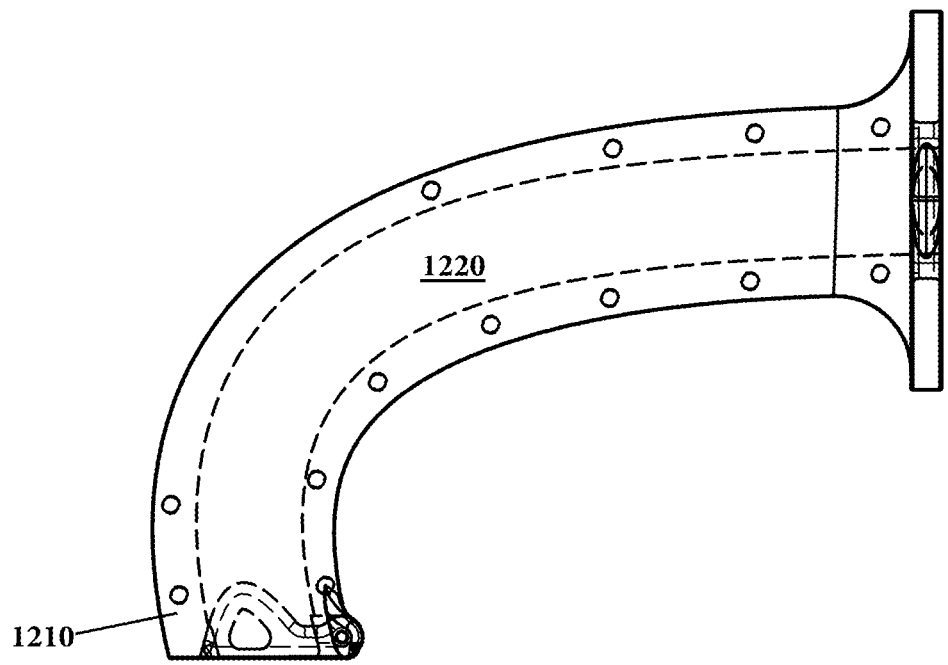
FIG. 11A a cross-section of the blind intubation device 1000 with the lever arm 1300 tucked into the tip 1210 of the device's 1000 cannulated stem 1200.
Figure 11B:
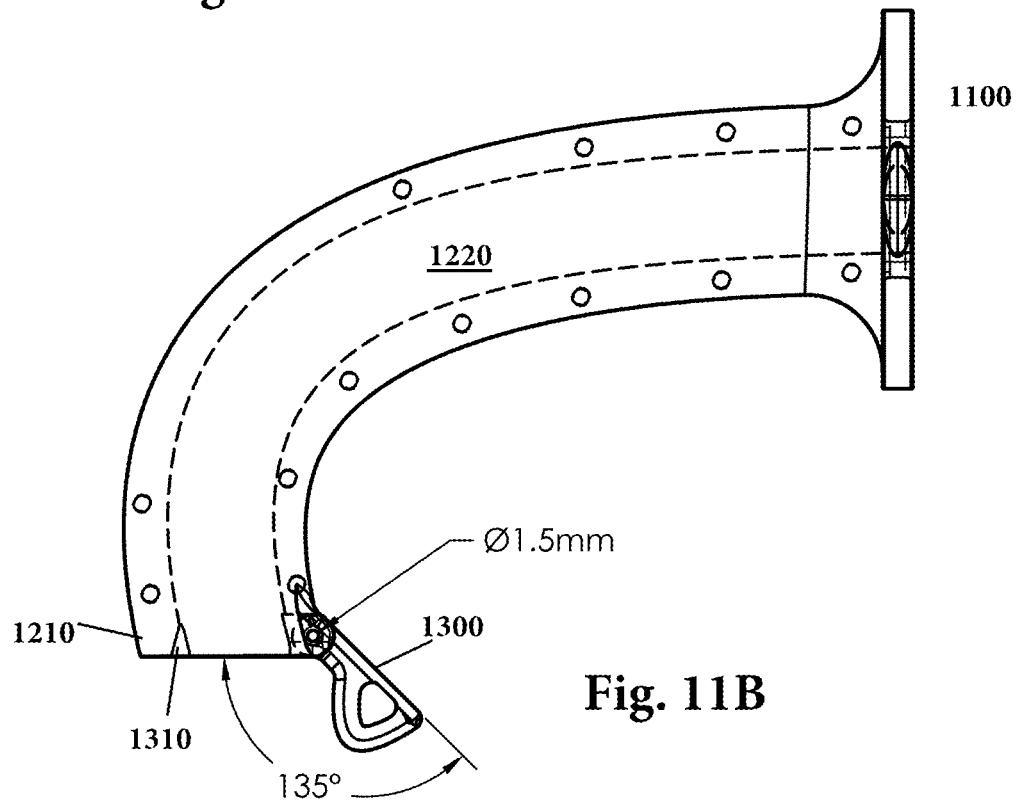
FIG. 11B a cross-section of the blind intubation device 1000 with the lever arm 1300 extended out of the tip 1210 of the device's 1000 cannulated stem 1200.
Figure 12A:
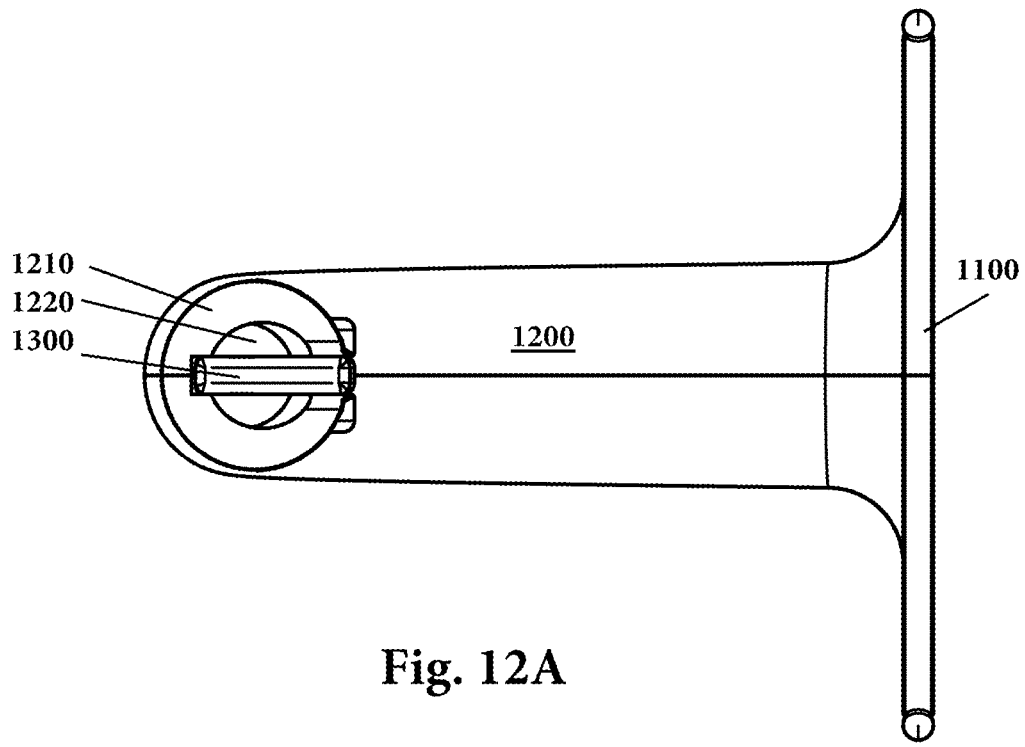
FIG. 12A a front view of the blind intubation device 1000 with the lever arm 1300 tucked into the tip 1210 of the device's 1000 cannulated stem 1200.
Figure 12B:
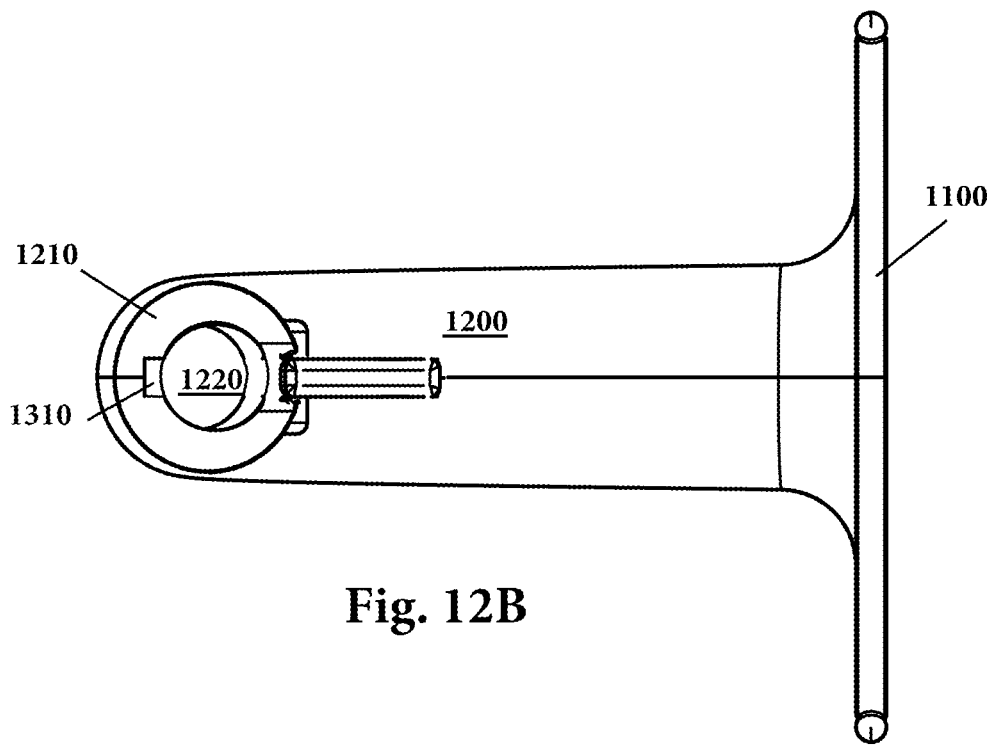
FIG. 12B a front view of the blind intubation device 1000 with the lever arm 1300 extended out of the tip 1210 of the device's 1000 cannulated stem 1200.
Figure 13A:
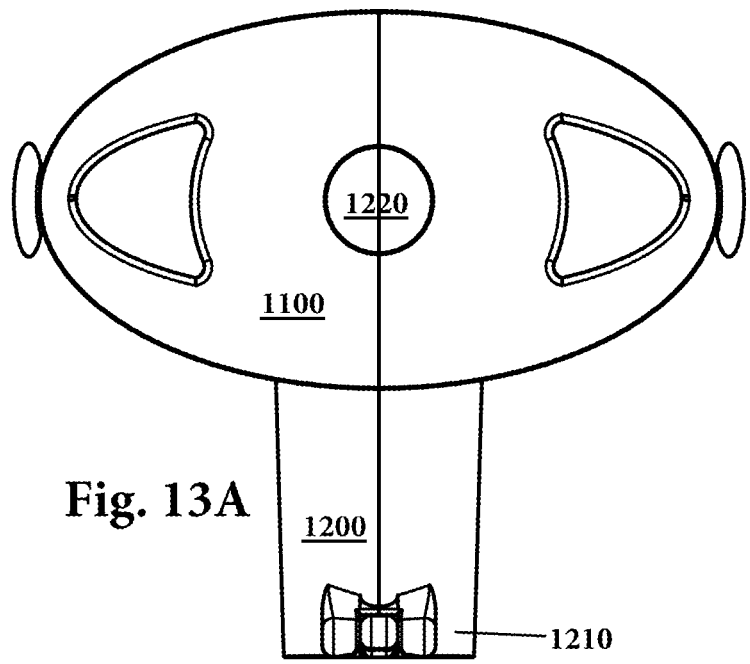
FIG. 13A a normal view of the blind intubation device 1000 with the lever arm 1300 tucked into the tip 1210 of the device's 1000 cannulated stem 1200.
Figure 13B:
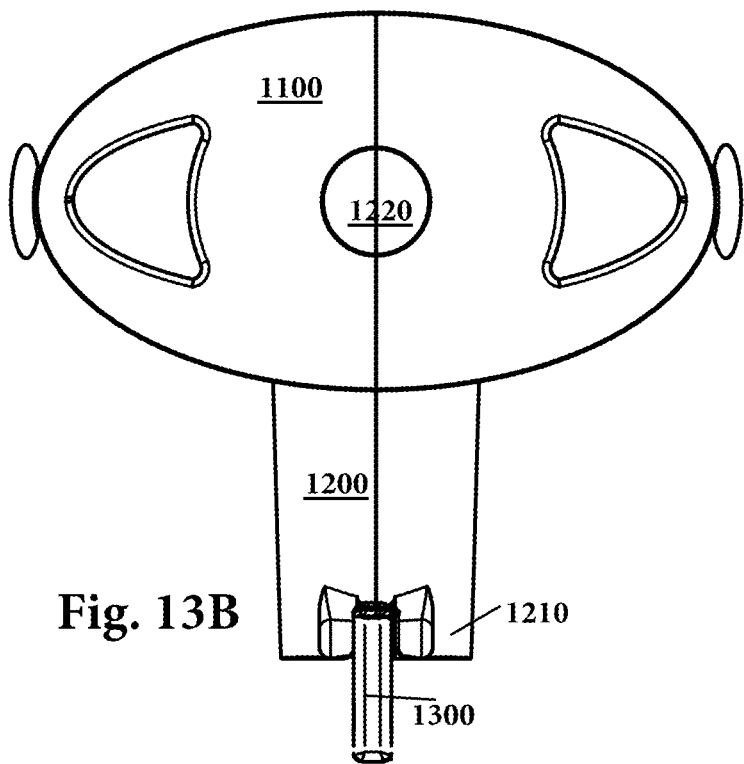
FIG. 13B a normal view of the blind intubation device 1000 with the lever arm 1300 extended out of the tip 1210 of the device's 1000 cannulated stem 1200.

FIG. 6 shows a schematic view of a lever arm 1300 (also called perforated pad). FIG. 7 shows a schematic view of the lever arm 1300. FIG. 8 shows a schematic view of the lever arm 1300. As discussed in greater detail below, the lever arm 1300 may be normally tucked into the tip of a cannulated stem and then extended out of the tip to hold back a patient's epiglottis so that a tube may be passed into the trachea of the patient.

FIGS. 9A, 10A, 11A, 12A, and 13A are various views of the blind intubation device 1000 with the lever arm 1300 tucked into the tip 1210 of the device's 1000 cannulated stem 1200. FIGS. 9B, 10B, 11B, 12B, and 13B are various views of the blind intubation device 1000 with the lever arm 1300 extended out of the tip 1210 of the device's 1000 cannulated stem 1200. Suitably, the lever arm 1300 may be spring loaded so that it is biased to a tucked position. As discussed below, the lever arm 1300 may be normally tucked into the tip 1210 of a cannulated stem 1200 and then extended out of the tip 1210 via the force of a tube (not shown) being passed through the airway 1220 of the stem 1200. When the lever arm 1300 is extended out of the tip 1210 it suitably serves to hold back a patient's epiglottis so that a tube may be passed into the trachea of the patient.

Figure 16:
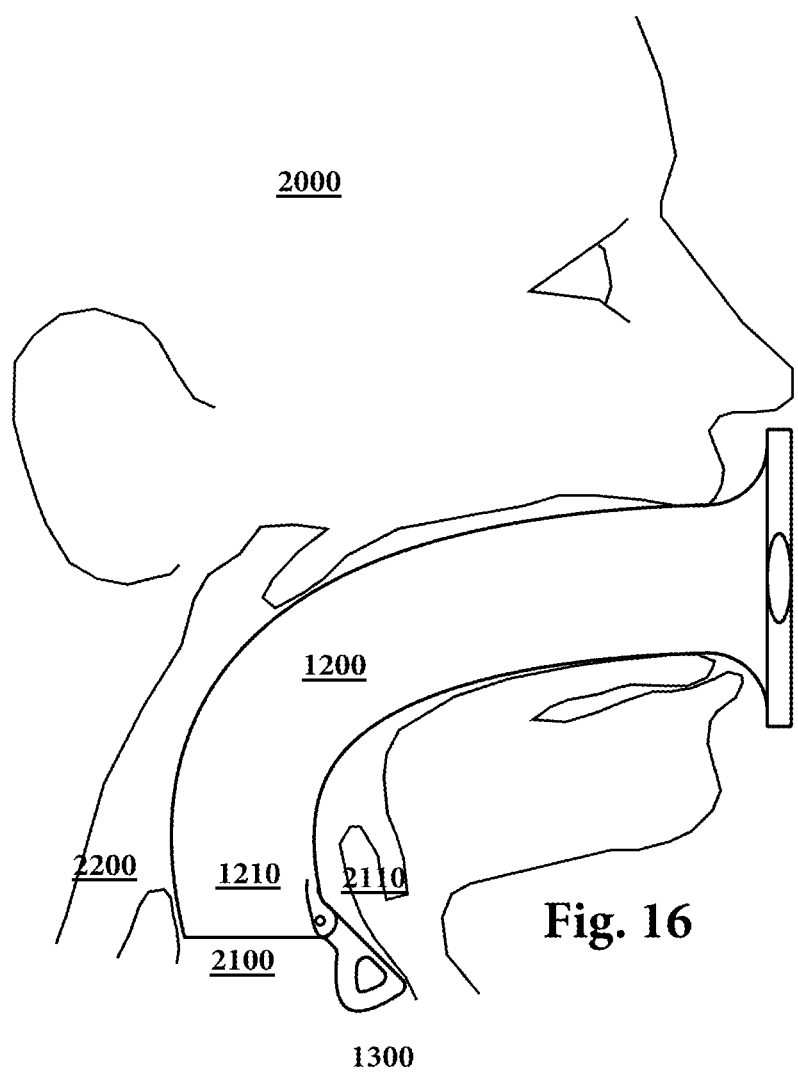
FIG. 16 is an environmental view of the blind intubation device 1000 inserted into a patient's 2000 throat with the curved cannulated stem 1200 turned downstream toward the patient's 2000 trachea 2100 and the lever arm 1300 extended from the tip 1210 of the stem 1200 so that it holds the epiglottis 2110 away from the tip 1210 of the stem 1200.

FIG. 16 is an environmental view of the blind intubation device 1000 inserted into a patient's 2000 throat with the curved cannulated stem 1200 turned downstream toward the patient's 2000 trachea 2100 and the lever arm 1300 extended from the tip 1210 of the stem 1200 so that it holds the epiglottis 2110 away from the tip 1210 of the stem 1200.

Figure 14:
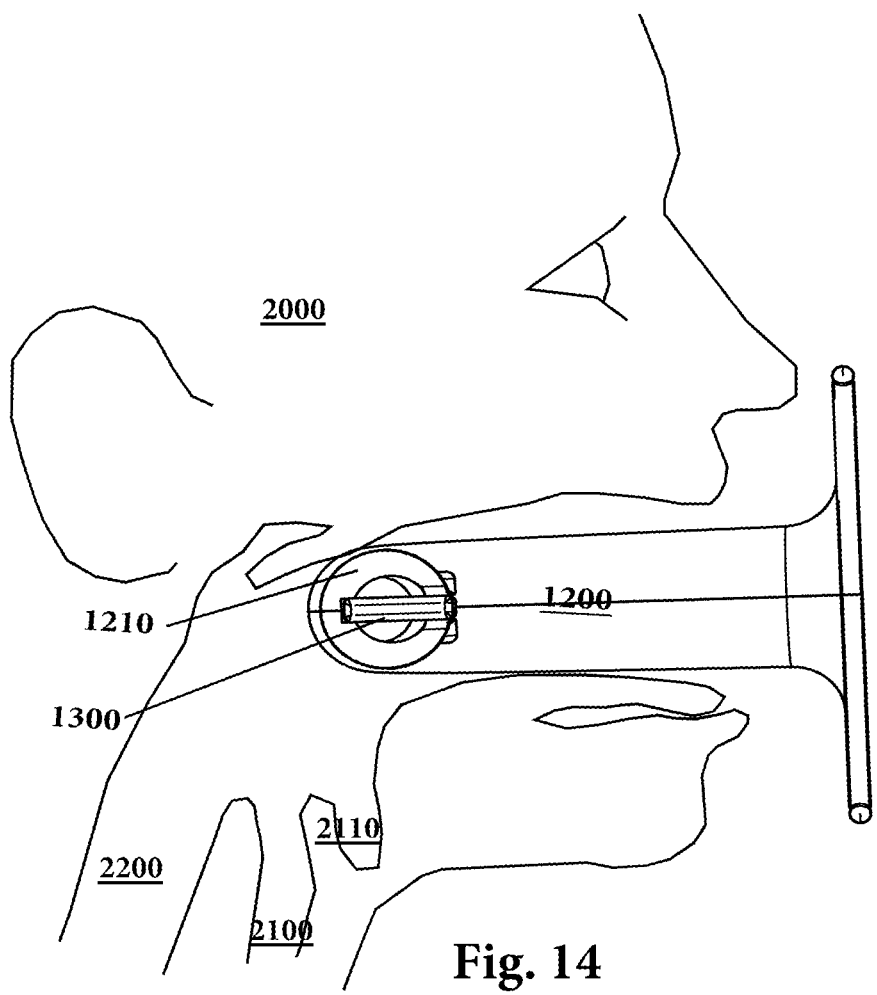
FIG. 14 is an environmental view of the blind intubation device 1000 inserted into a patient's 2000 throat with the curved cannulated stem 1200 orthogonal to the patient's 2000 trachea 2100.
Figure 15:
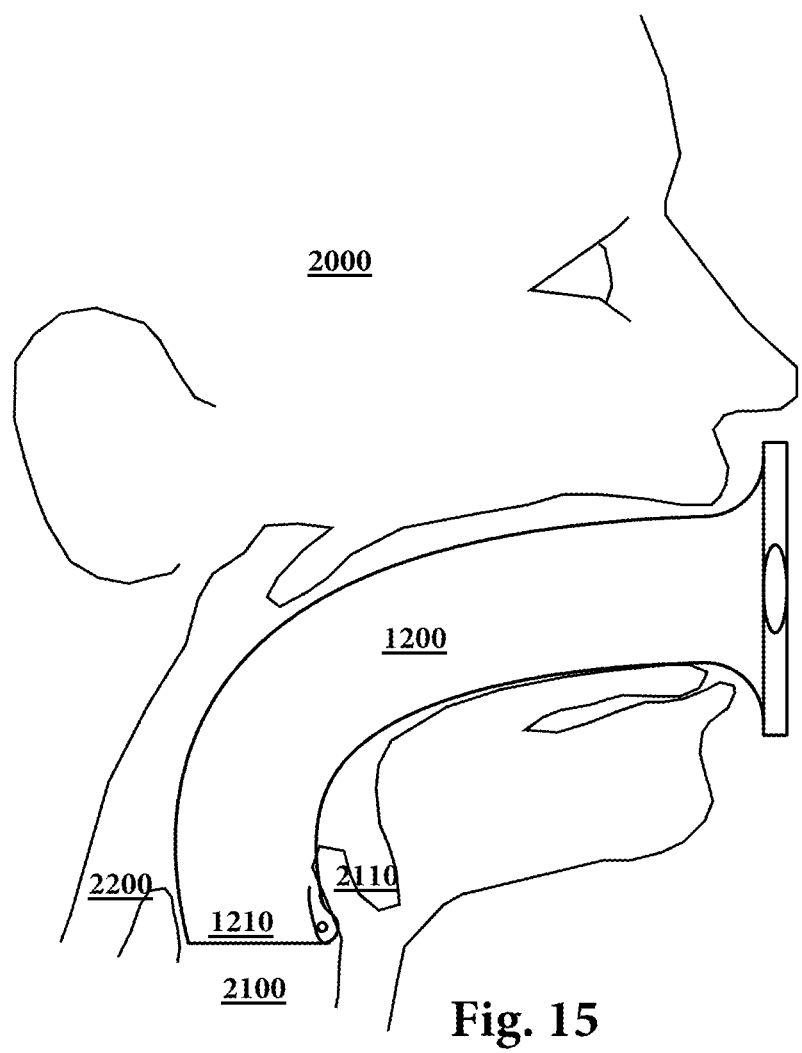
FIG. 15 is an environmental view of the blind intubation device 1000 inserted into a patient's 2000 throat with the curved cannulated stem 1200 turned downstream toward the patient's 2000 trachea 2100.

FIGS. 14 through 16 illustrate a preferred method. In accordance with the present method and apparatus 1000 of inserting endotracheal tubes into the patient's 2000 airway 2100, the patient 2000 is first placed in a prone or substantially equivalent position. The patient's 2000 mouth must be accessible to the physician or technician (not shown) inserting an endotracheal tube (not shown). Once the patient 2000 is in the proper position, the mouth is opened and the patient's 2000 head tilted slightly in an attempt to straighten the passageway 2100 from the rear of the mouth to the desired tracheal depth.

Still referring to FIGS. 14-16, the curved cannulated stem 1200 of the funnel may then be inserted into the mouth of the patient, preferably but not necessarily with the curvature of the cannulated stem (hook) being orthogonal to the inside of the patient's cheek before being rotated into position. FIG. 14 is an environmental view of the blind intubation device 1000 inserted into a patient's 2000 throat with the curved cannulated stem 1200 orthogonal to the patient's 2000 trachea 2100. The cannulated stem 1200 may have the endotracheal tube (not shown) already partially inserted, or insertion may take place after the airway 2100 has been properly fitted with the device 100 as shown in FIG. 15. FIG. 15 is an environmental view of the blind intubation device 1000 inserted into a patient's 2000 throat with the curved cannulated stem 1200 turned downstream toward the patient's 2000 trachea 2100. During rotation of the device into position (e.g., from FIGS. 14 to 15), the hook, i.e. curved cannulated stem 1200, may be downstream so that the tip 1210 of the stem is toward the patient's lungs. Ultimately, the endotracheal tube (not shown) may be guided past the soft palate and pharynx until it rests fully inserted into the patient's throat 2100.

Referring now to FIG. 16, the endotracheal tube (not shown) depresses outward as it moves through the tip 1210 of the stem 1200 a perforated pad or lever arm 1300. When so depressed outward, the pad or lever arm 1300 holds the epiglottis 2110 in place as to reduce the likelihood of esophageal insertion. The cannulated stem 1200 may be constructed with a curve to safely direct the tube away from the esophagus 2200 and into the trachea 2100 at a reduced risk of damage to other part of the anatomy and respiratory function. A ventilating means, such as an external bladder or machine lung (not shown), is attached the exposed end and funnel portion 1100 of the device 1000.

The manner in which the cannulated stem 1200 is inserted greatly reduces the risk of esophageal insertion of the endotracheal tube and thus the risks associated with improper respiration. Some of the associated risks include brain damage, cardiac arrest, and death. Use of the cannulated stem and method at hand likewise reduces the risk of aspiration of the stomach or improper lung aspiration and associated risks. Additionally, the simplicity of the apparatus typically allows for intubation in substantially less time than traditional methods.

Figure 17:
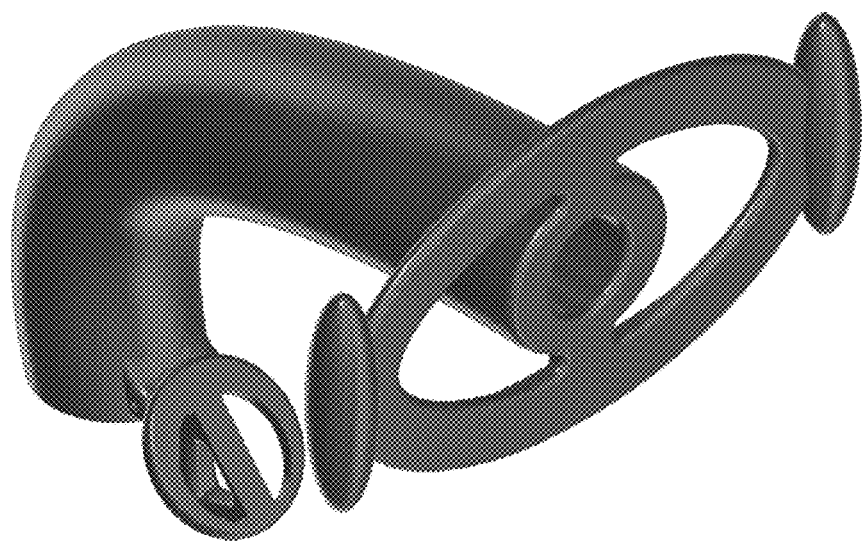
FIG. 17 is a fully rendered isometric view of another embodiment of a blind intubation device.
Figure 18:
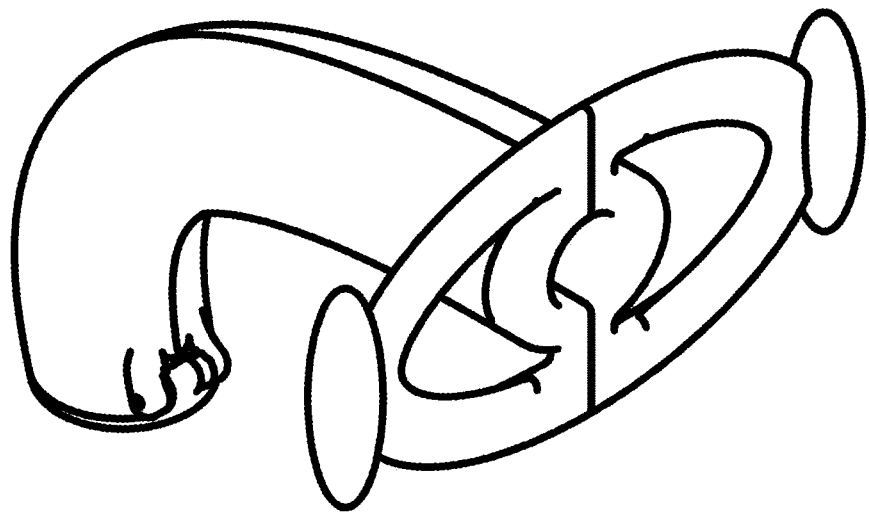
FIG. 18 is an isometric schematic view of the blind intubation device.
Figure 19:
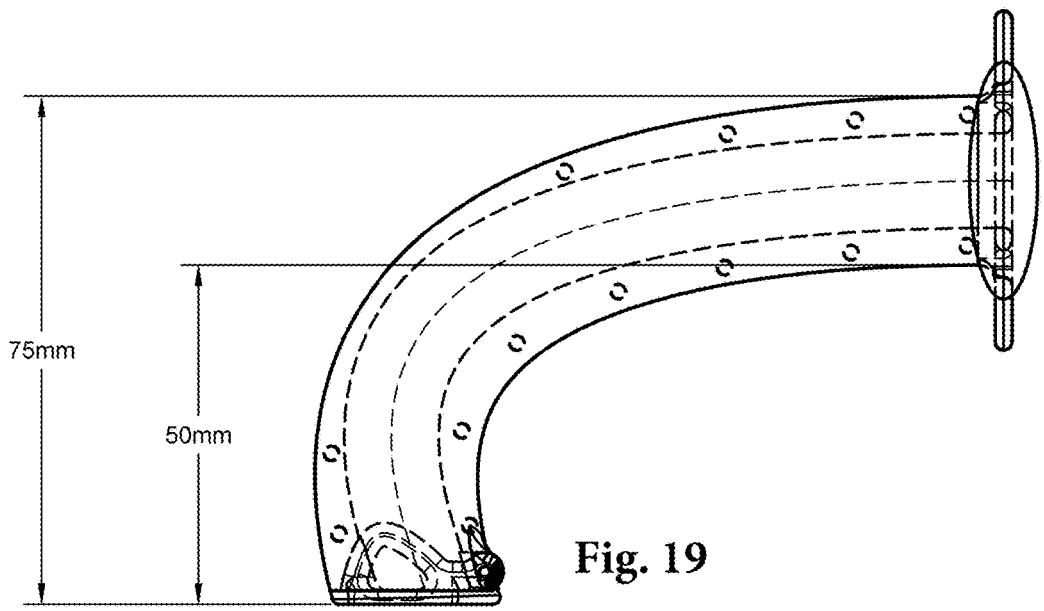
FIG. 19 is a cross-sectional side view of the blind intubation device.
Figure 20:
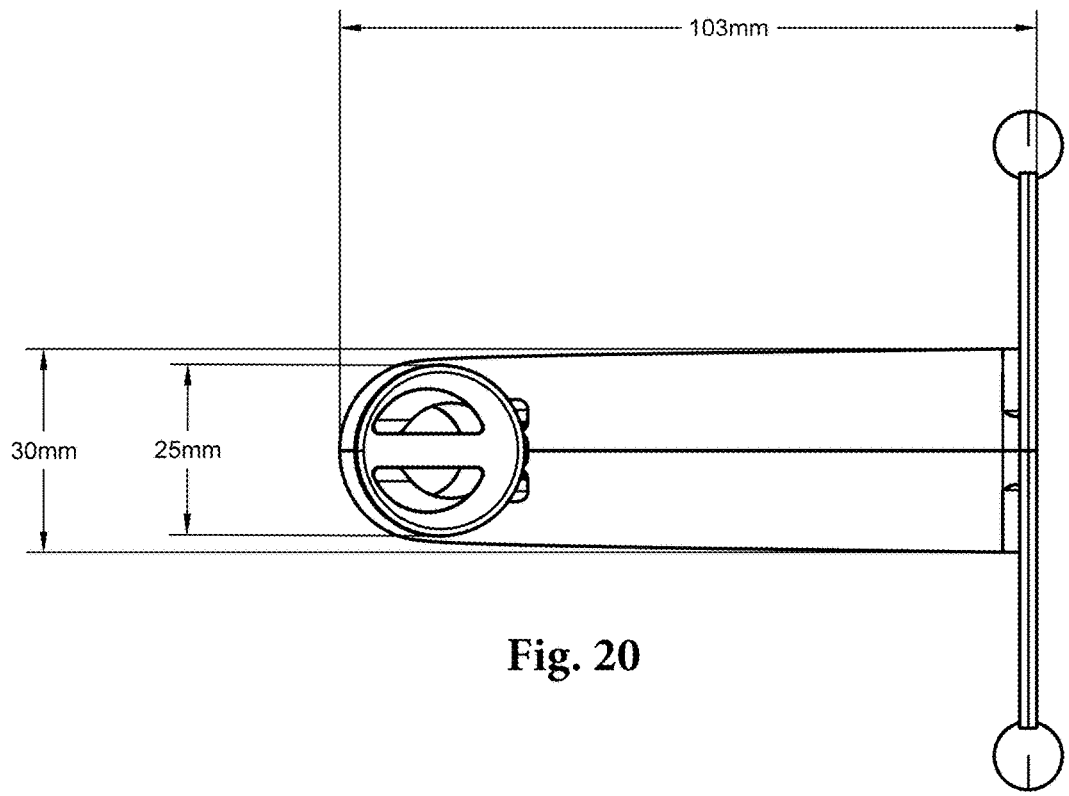
FIG. 20 is front view of the blind intubation device.

FIG. 17 is a fully rendered isometric view of another embodiment of a blind intubation device. FIG. 17 shows a perforated pad fitted to the hooked end of the cannulated stem in the engaged position and funnel with wings fitted to the opposite end of the stem. FIG. 18 is an isometric schematic view of the blind intubation device. FIG. 18 shows the perforated pad in the disengaged position. FIG. 19 is a cross-sectional side view of the blind intubation device. FIG. 19 shows that the stem tucks away the perforated pad. FIG. 19 also shows the perforated pad in the disengaged position as well as the general contour and dimensions of the cavities within the airway associated with a particular embodiment. FIG. 20 is front view of the blind intubation device. FIG. 20 shows the perforated pad in the disengaged position and the funnel's dimensions and respective positions in this embodiment. FIG. 21 is a normal view of the blind intubation device. FIG. 21 is a schematic normal to the plane on which the funnel of this particular embodiment of cannulated stem lie. This view of FIG. 21 shows an embodiment in which the fitting means employed to fix the perforated flap is a traditional hinge utilizing a spring as an engagement means.

Figure 25:
FIG. 25 is a side view of the blind intubation device with the lever arm extended out of the tip of the device's cannulated stem.
Figure 26:
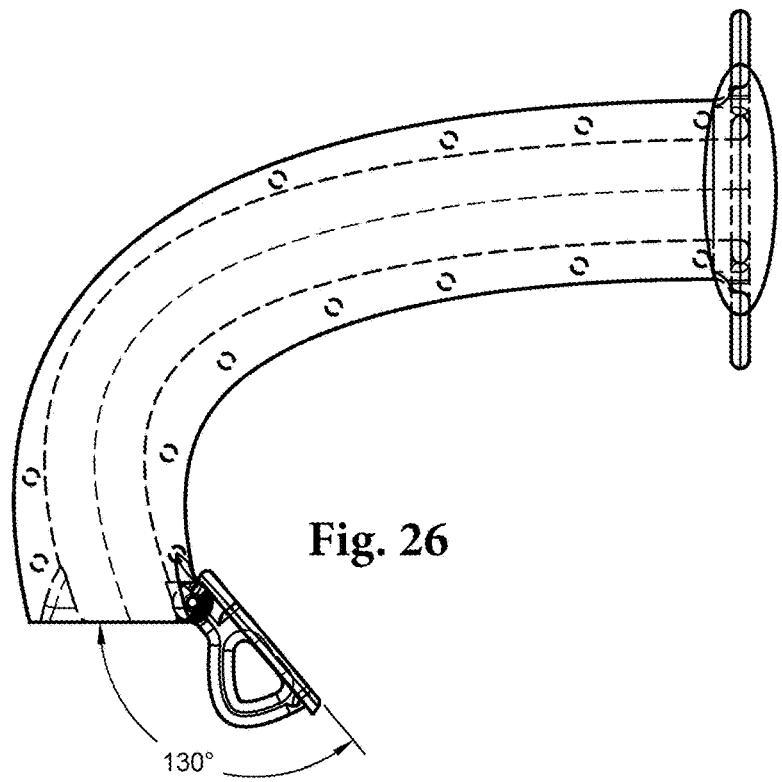
FIG. 26 is a cross-section of the blind intubation device with the lever arm extended out of the tip of the device's cannulated stem.

FIG. 22 shows a schematic view of another embodiment of a lever arm (also called perforated pad). FIG. 23 shows a schematic view of the lever arm. FIG. 24 shows a schematic view of the lever arm. This particular embodiment uses a pad with two large holes. Other embodiments may employ a different number or different shapes of holes. FIG. 25 is a side view of the blind intubation device with the lever arm extended out of the tip of the device's cannulated stem. FIG. 26 is a cross-section of the blind intubation device with the lever arm extended out of the tip of the device's cannulated stem.

Figure 27:
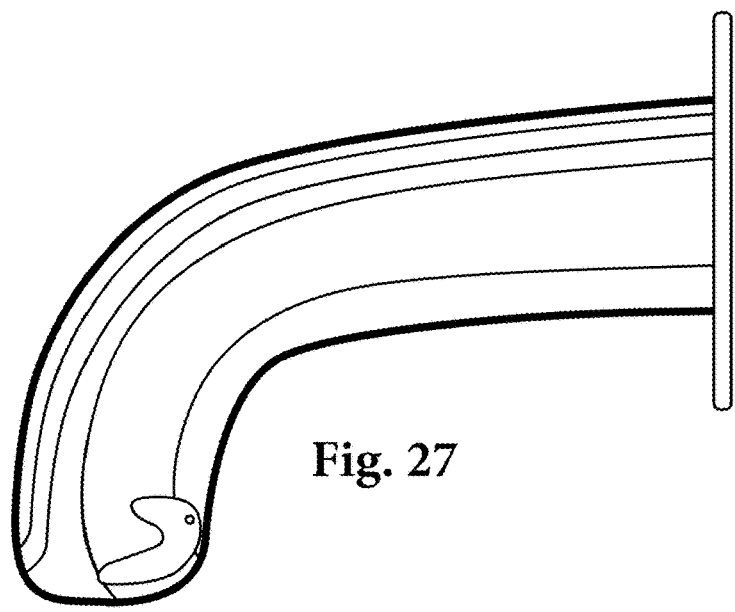
FIG. 27 is a cross-sectional side view of the blind intubation device.
Figure 28:
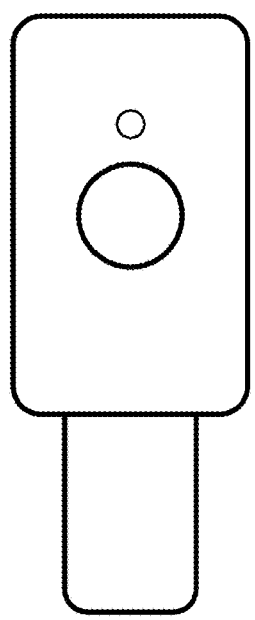
FIG. 28 is a normal view of the blind intubation device.

FIG. 27 is a cross-sectional side view of another alternate embodiment of a blind intubation device. FIG. 28 is a normal view of the blind intubation device.

FIG. 29 is a perspective view of a tube clamp 1500. Suitably, the clamp 1500 may be installed over the canal 1220 of a blind intubation device 1000 to ensure a tube 3000 (FIG. 31) is not accidentally provided too deep into a trachea 2100 during installation or afterward. FIG. 30 is a normal view of the blind intubation device 1000 with a tube clamp 1500 installed on the canal 1220 and the lever arm 1300 extended out of the tip 1210 of the device's 1000 cannulated stem 1200. FIG. 31 is an environmental view of the blind intubation device 1000 inserted into a patient's 2000 throat with the curved cannulated stem 1200 turned downstream toward the patient's 2000 trachea 2100, the lever arm 1300 extended from the tip 1210 of the stem 1200 so that it holds the epiglottis 2110 away from the tip 1210 of the stem 1200, a tube clamp 1500 installed on the canal 1220 with a tube 3000 inserted into the canal 1220 and there held fast by the clamp 1500.

Other assembly methods may be practiced depending on the use of alternative embodiments described herein, and will be readily apparent to those skilled in the art.

In one preferred embodiment, the engagement means comprises a spring or spring-like feature which pushes on the perforated pad, causing said pad to swivel and make contact with the epiglottis.

In some preferred embodiments, the eccentricity of the airway's curvature will vary as to allow for use on patients with varying throat dimensions.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

PAPER "SEQUENCE LISTING"

Not applicable.

I claim:

1. A method for endotracheal intubation comprising the steps of:
    obtaining an apparatus comprising
        a funnel with a curved cannulated stem that is configured for oral insertion into a patients throat;
        a lever arm that is tucked into a tip of the curved cannulated stem so that a nub of the lever arm is disposed within the curved cannulated stem;
    obtaining an endotracheal tube;
    opening a patient's mouth;
    inserting the curved cannulated stem, tip-first, into the patient's mouth;
    manipulating the positioning of said curved cannulated stem as to allow for its passage into the patient's throat;
    ensuring the curved cannulated stem is fully inserted into the patient's throat;
    passing the endotracheal tube through said funnel and curved cannulated stem to press the nub of the lever arm so that the lever arm extends out of the tip into contact with the patient's epiglottis wherein the endotracheal tube is directed by the curved cannulated stem away from the patient's esophagus and into the patient's trachea;
    ensuring that an end of the endotracheal tube is exposed at the funnel and outside the patient's mouth;
    attaching a ventilating means to the exposed end of the endotracheal tube; and
    ventilating the patient's lungs with the ventilating means.

2. The method of claim 1, wherein the ventilation means comprises an external bladder or an automated machine lung.

3. The method of claim 1, wherein the curved cannulated stem is inserted in a rotated position and then counter-rotated once in the patient's mouth as to facilitate passage into the patient's throat.

4. The method of claim 1, wherein the curved cannulated stem is inserted to a depth within the patient's throat while gripping wings that are fixed to the periphery of the funnel remain outside of the patient's mouth.

5. The method of claim 1 wherein the lever arm is rotatably fixed to the tip of the cannulated stem via a hinge so that the lever arm pivots about the hinge from a tucked-in position to an extended position during the step of passing the endotracheal tube through said funnel and curved cannulated stem to press the nub of the lever arm so that the lever arm extends out of the tip into contact with the patient's epiglottis wherein the endotracheal tube is directed by the curved cannulated stem away from the patient's esophagus and into the patient's trachea.

6. The method of claim 5 wherein the lever arm is situated in the tucked-in position at an angle of zero degrees relative to a plane defined by the tip of the curved cannulated stem.

7. The method of claim 6 wherein the lever arm is situated in the extended position at an angle of one hundred and thirty-five degrees relative to a plane defined by the tip of the curved cannulated stem.

* * * * *